United States Patent
Graham et al.

(10) Patent No.: US 7,635,867 B2
(45) Date of Patent: Dec. 22, 2009

(54) NANOTUBE ARRAY AND METHOD FOR PRODUCING A NANOTUBE ARRAY

(75) Inventors: Andrew Graham, München (DE); Franz Hofmann, München (DE); Johannes Kretz, München (DE); Franz Kreupl, München (DE); Richard Luyken, München (DE); Wolfgang Rösner, Ottobrunn (DE)

(73) Assignee: Infineon Technologies AG (DE)

( * ) Notice: Subject to any disclaimer, the term of this patent is extended or adjusted under 35 U.S.C. 154(b) by 236 days.

(21) Appl. No.: 10/476,663

(22) PCT Filed: May 16, 2002

(86) PCT No.: PCT/EP02/05433

§ 371 (c)(1),
(2), (4) Date: May 14, 2004

(87) PCT Pub. No.: WO02/092505

PCT Pub. Date: Nov. 21, 2002

(65) Prior Publication Data

US 2004/0232426 A1      Nov. 25, 2004

(30) Foreign Application Priority Data

May 16, 2001   (DE) .............................. 101 23 876

(51) Int. Cl.
*H01L 31/0312* (2006.01)
(52) U.S. Cl. ................. 257/77; 257/419; 257/E29.137
(58) Field of Classification Search ............ 252/77, 252/419, 324, 76, 79, 46, 44, 325; 257/78, 257/368, 40, 77, 213, 401, 419, E29.137; 977/238
See application file for complete search history.

(56) References Cited

U.S. PATENT DOCUMENTS 6,297,063 B1 * 10/2001 Brown et al. .................... 438/2

(Continued)

FOREIGN PATENT DOCUMENTS

EP         0 913 508      *    5/1999

(Continued)

OTHER PUBLICATIONS

Harris, PJF (1999), "Carbon Nanotubes and Related Structures—New Materials for the Twenty-first Century", Cambridge University Press, Cambridge.

(Continued)

*Primary Examiner*—Thomas L Dickey
*Assistant Examiner*—Fazli Erdem
(74) *Attorney, Agent, or Firm*—Altera Law Group, LLC

(57) ABSTRACT

A nanotube array and a method for producing a nanotube array. The nanotube array has a substrate, a catalyst layer, which includes one or more subregions, on the surface of the substrate and at least one nanotube arranged on the surface of the catalyst layer, parallel to the surface of the substrate. The at least one nanotube being arranged parallel to the surface of the substrate results in a planar arrangement of at least one nanotube. Therefore, the nanotube array of the invention is suitable for coupling to conventional silicon microelectronics. Therefore, according to the invention it is possible for a nanotube array to be electronically coupled to macroscopic semiconductor electronics. Furthermore, the nanotube array according to the invention may have an electrically insulating layer between the substrate and the catalyst layer. This electrically insulating layer preferably has a topography which is such that the at least one nanotube rests on the electrically insulating layer at its end sections and is uncovered in its central section. As a result of the surface of the at least one nanotube being partly uncovered, the uncovered surface of the nanotube can be used as an active sensor surface. For example, the uncovered surface of the nanotube can come into operative contact with an atmosphere which surrounds the nanotube array. The electrical resistance of a nanotube changes significantly in the presence of certain gases. Thus because the nanotube is clear and uncovered, the nanotube array can be used in many sensor applications.

14 Claims, 10 Drawing Sheets

U.S. PATENT DOCUMENTS

| | | | |
|---|---|---|---|
| 6,350,488 B1 * | 2/2002 | Lee et al. | 427/249.1 |
| 6,628,053 B1 * | 9/2003 | Den et al. | 313/310 |
| 6,863,942 B2 * | 3/2005 | Ren et al. | 428/36.9 |
| 2002/0014667 A1 * | 2/2002 | Shin et al. | 257/368 |

FOREIGN PATENT DOCUMENTS

| | | |
|---|---|---|
| JP | 09228160 | 9/1997 |
| JP | 11139815 | 5/1999 |
| JP | 11194134 | 7/1999 |
| JP | 2001-177052 | 6/2001 |
| JP | 2001218578 | 8/2001 |
| JP | 2002118248 | 4/2002 |
| WO | WO/01/44796 | 6/2001 |

OTHER PUBLICATIONS

Dekker, C., et al., (1999), "Carbon Nanotubes as Molecular Quantum Wires", Physics Today 5/99:22-28.

Kong, J., et al.. (2000), "Nanotube Molecular Wires as Chemical Sensors", Science 287:622-625.

Fan, Sr., et al. (1999), "Self-Oriented Regular Arrays of Carbon Nanotubes and Their Field Emission Properties". Science 283:512-514.

Suh, J., et al., (1999), "Highly ordered two-dimensional carbon nanotube arrays", ApplPhysLett. 75/14:2047-2049.

Soh, H.T., et al.. "Integrated nanotube circuits: Controlled growth and ohmic contacting of single-walled carbon nanotubes", Applied Physics Letters 75(5):627-629.

Kong, et al. "Synthesis of individual single-walled carbon nanotubes on patterned silicon wafers", Nature/vol. 395, Oct. 29, 1998, pp. 878-881.

Li, Jr., et al.. "Highly-ordered carbon nanotube arrays for electronics applications". 1999 American Institute of Physics, pp. 367-369.

* cited by examiner

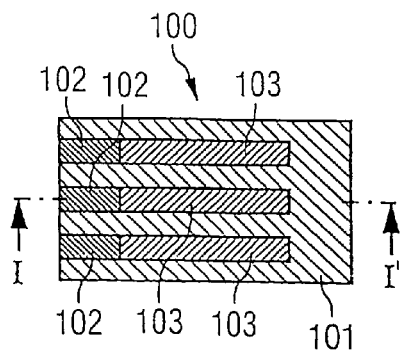
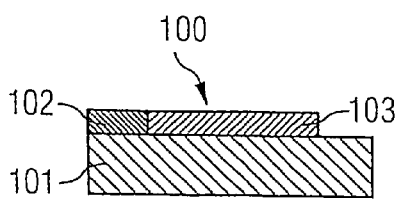
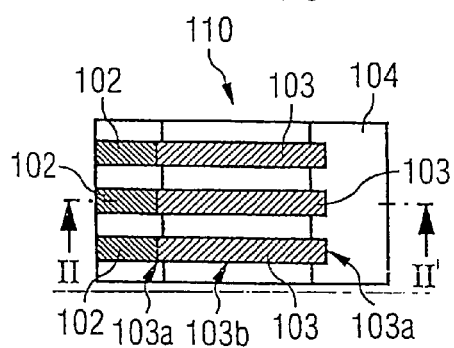
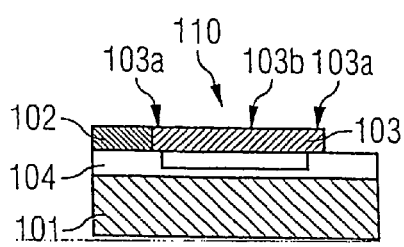
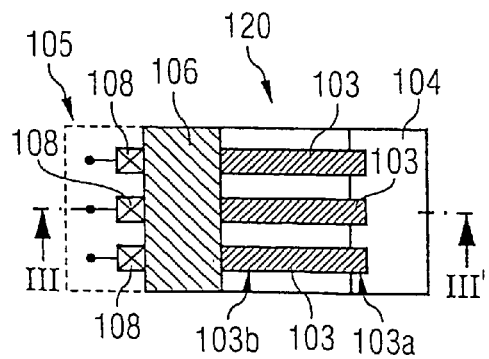
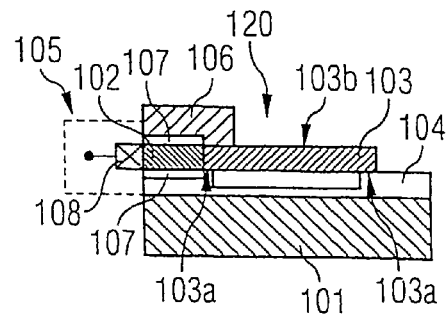

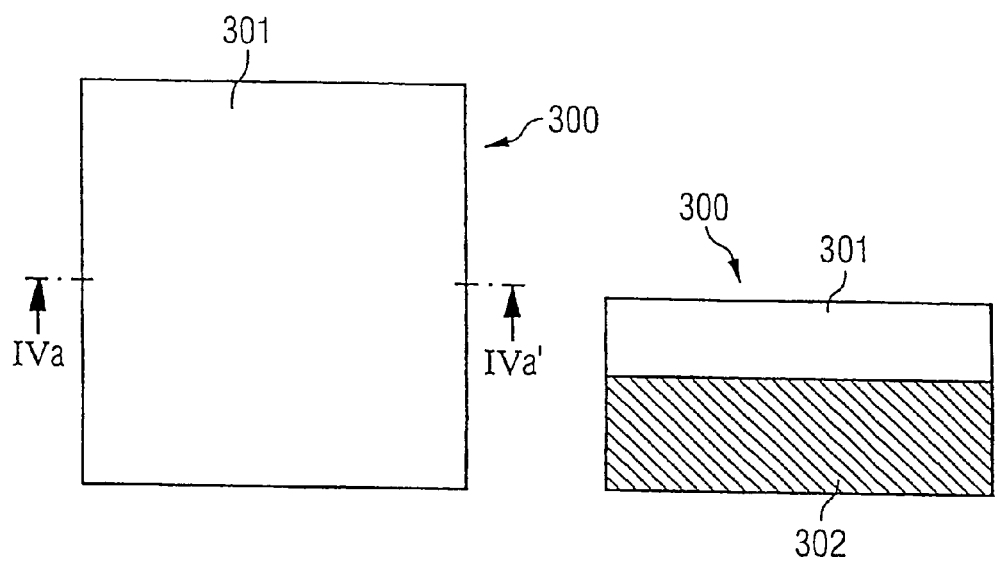
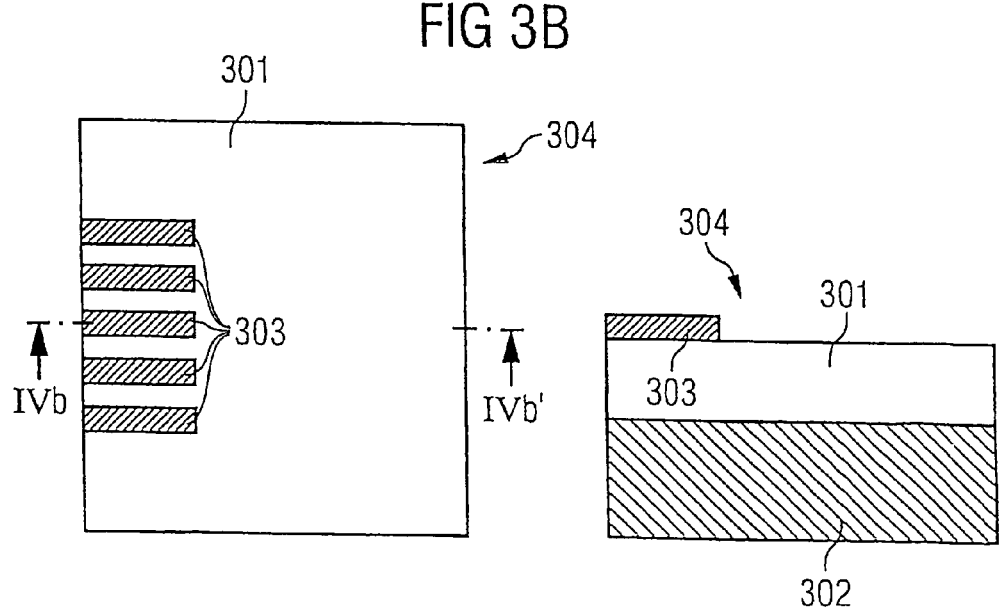

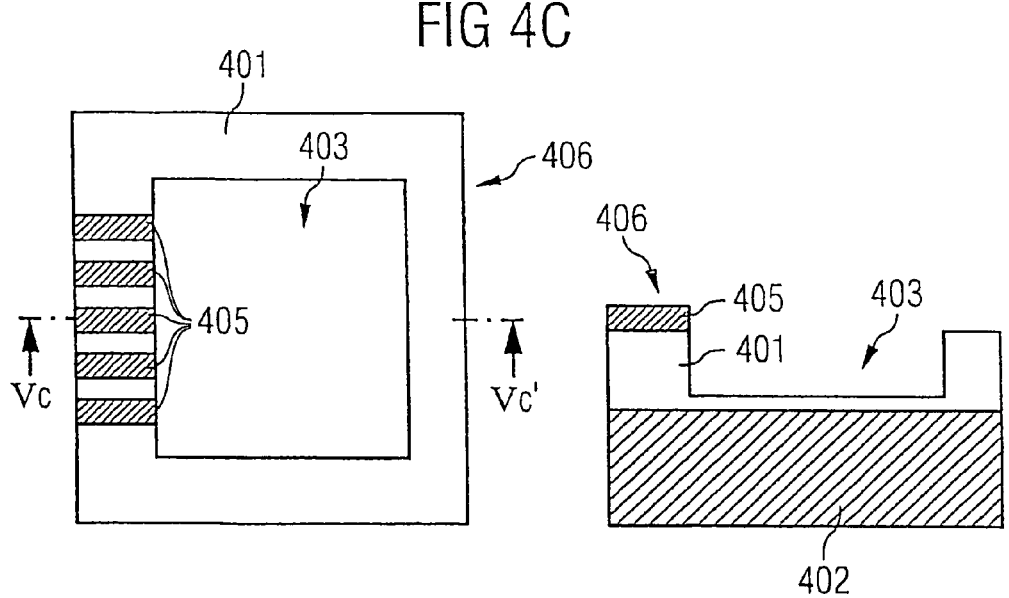
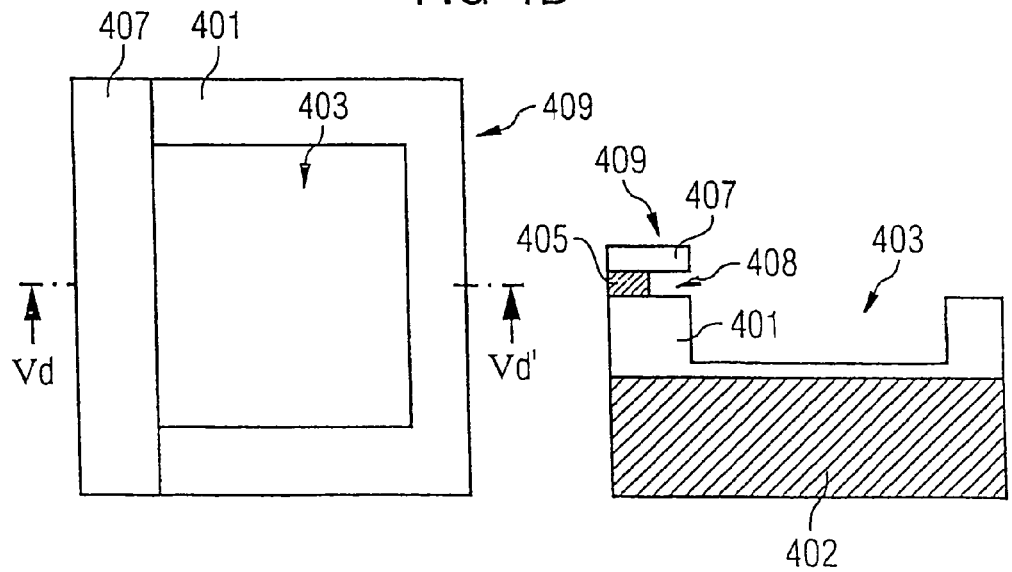

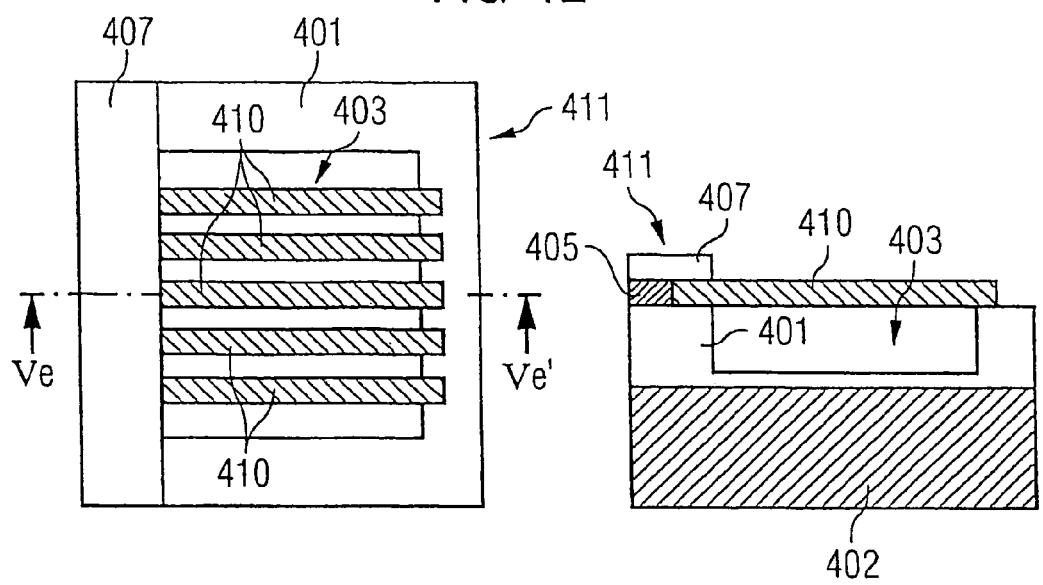

NANOTUBE ARRAY AND METHOD FOR PRODUCING A NANOTUBE ARRAY

BACKGROUND OF THE INVENTION

1. Field of the Invention

The invention relates to a nanotube array and to a method for producing a nanotube array.

As ongoing miniaturization continues, conventional silicon microelectronics will reach its limit. In particular, in the next ten years the development of ever smaller and more densely arranged transistors, which by now amount to several hundred millions of transistors per chip, will in principle encounter physical problems and limits. When feature sizes drop below 80 nm, the components will be disruptively affected by quantum effects, and these effects will become dominant at feature sizes of approximately 30 nm. The increasing integration density of the components on a chip also leads to a dramatic increase in the waste heat which is generated.

2. Description of the Related Prior Art

Carbon nanotubes are known to be a possible successor technology to conventional semiconductor electronics. By way of example, [1] gives an overview of this technology.

A nanotube is a single-walled or multiwalled, tube-like carbon compound. In the case of multiwalled nanotubes, at least one inner nanotube is coaxially surrounded by an outer nanotube. Single-walled nanotubes typically have diameters of approximately one nanometer, while the length of a nanotube may be several hundreds of nanometers. The ends of a nanotube are often closed off by means of in each case half a part of a fullerene molecule.

The extended π-electron system and the geometric structure of nanotubes result in good electrical conductivity, and consequently nanotubes are suitable for the construction of circuits with dimensions in the nanometer range. It is known from [2] that the electrical conductivity of carbon nanotubes may significantly exceed that of metals of the same dimensions.

The diameter and chirality of a nanotube are parameters on which the electrical conductivity of the nanotube is dependent. The electrical conductivity of a nanotube may furthermore be altered by applying an electric field and/or doping the nanotubes with boron nitride. In the latter case, it is customary to refer to a nanotube doped with boron atoms and nitrogen atoms or to a boron nitride nanotube.

On account of the conductivity of nanotubes and on account of the possibility of adjusting this conductivity in the manner described above, nanotubes are suitable for a wide range of applications, for example for the electrical connection technology in integrated circuits, for microelectronics components and for electron emitters.

Furthermore, it is known from [3] that the electrical resistance of nanotubes changes by approximately three orders of magnitude within a few seconds if nanotubes are exposed to a gas, such as for example a nitrogen dioxide ($NO_2$) gas or an ammonia ($NH_3$) gas. In an $NH_3$ atmosphere, the electrical conductivity of the nanotubes is reduced, which can be explained by a shift in the valence band edge to well below the Fermi level of the nanotubes with a resultant charge carrier depletion. Conversely, the electrical conductivity of the nanotubes rises by approximately three orders of magnitude if the nanotubes are exposed to an $NO_2$ atmosphere in a concentration of approximately 200 ppm. This can be explained by the fact that the Fermi energy of the nanotubes is shifted closer to the valence band and accordingly the number of charge carriers in the nanotubes increases.

For nanotubes to be used in microelectronics, it is often desirable for nanotubes to be applied in a defined manner at specific locations of a substrate. By way of example, nanotubes can be used as conductors in order to couple two conductor levels of a microcircuit element which are electrically separated from one another. For this purpose, it is necessary for nanotubes to be grown only where a corresponding electric coupling is desired, whereas the other regions of the substrate should remain clear of nanotubes in order to prevent electrical short circuits.

To achieve this objective, it is known to use a sputtering process to apply a metal which catalyzes the growth of nanotubes, for example iron, to a substrate which has been patterned, for example, with photoresist. Then, the patterned photoresist and the metal located thereon are removed using a lift-off method. As a result, the metal material remains only on locations on the substrate which were previously uncovered. The catalytically active metal which remains is used as a matrix for nanotubes to grow on.

Vapor deposition processes (chemical vapor deposition, CVD) are known processes for the production of carbon nanotubes. In the CVD process, the components and dopants are brought together as gases, if appropriate with additional carrier gases, in a reaction space, where the deposition on the substrate takes place. To produce carbon nanotubes using the CVD process, the carbon source used is often methane ($CH_4$) or alternatively acetylene ($C_2H_2$).

Methods for producing nanotubes and nanowires on catalytically active surfaces using the CVD process have been described, for example, in [4] and [5]. The method described in those documents makes it possible to produce carbon nanotubes which are arranged vertically on a substrate.

However, in the method which is described in [4], the base has to consist of aluminum. This is a disadvantageous restriction in terms of the material. Furthermore, the method described in [4] results in relatively large, multiwalled carbon nanotubes with diameters of approximately 50 nm. Also, the carbon nanotubes produced using the method described are oriented perpendicular to the substrate and can therefore only be integrated in conventional silicon microelectronics to a limited extent.

The method for producing carbon nanotubes which is described in [5] results in the formation of an arrangement of carbon nanotubes in densely packed blocks. These blocks are defined by the catalyst (for example iron) which has been vaporized on by means of a mask. However, it is difficult to produce a regular arrangement using the production method described. Since once again it is only possible to produce nanotubes which are oriented perpendicular to the surface of the substrate, there are considerable limitations to the way in which the nanotubes can be coupled to conventional silicon microelectronics.

To summarize, methods for producing an array of carbon nanotubes which are known from the prior art have a number of drawbacks. For example, the nanotubes produced using the methods described are oriented perpendicular to the surface of the substrate. Furthermore, according to the known methods it is difficult to produce structurally defined arrays of nanotubes. There is no precisely defined direction of growth for the nanotubes on the surface of a catalyst material. The lack of order which results and the fact that the nanotubes are oriented perpendicular to the substrate surface means that the nanotube arrays which are known from the prior art cannot be coupled to conventional silicon microelectronics or can only do so with difficulty.

It is known from [6] to form catalyst islands on a substrate. A carbon nanotube which is coupled to two catalyst islands can be formed using a CVD process if a carbon nanotube which grows from a catalyst island happens randomly to grow toward a second catalyst island. Therefore, once again according to [6] it is not possible to produce a spatially sufficiently well defined array of nanotubes.

BRIEF SUMMARY OF THE INVENTION

The invention is based on the problem of providing a spatially well defined array of planar-oriented nanotubes.

The problem is solved by a nanotube array and a method for producing a nanotube array having the features of the independent patent claims.

A nanotube array has a substrate, a catalyst layer, which includes one or more subregions, on the surface of the substrate and at least one nanotube arranged on the surface of the catalyst layer, parallel to the surface of the substrate.

The at least one nanotube being arranged parallel to the surface of the substrate results in a planar arrangement of at least one nanotube. Therefore, the nanotube array of the invention is suitable for coupling to conventional silicon microelectronics. Therefore, according to the invention it is possible for a nanotube array to be electronically coupled to macroscopic semiconductor electronics.

Furthermore, the nanotube array according to the invention may have an electrically insulating layer between the substrate and the catalyst layer. This electrically insulating layer preferably has a topography which is such that the at least one nanotube rests on the electrically insulating layer at its end sections and is uncovered in its central section.

As a result of the surface of the at least one nanotube being partly uncovered, the uncovered surface of the nanotube can be used as an active sensor surface. By way of example, the uncovered surface of the nanotube can come into operative contact with an atmosphere which surrounds the nanotube array. As has been stated above, the electrical resistance of a nanotube changes significantly in the presence of certain gases (for example $NO_2$ or $NH_3$), with the result that, on account of the nanotube being clear and uncovered, the nanotube array can be used in many sensor applications.

Furthermore, in the nanotube array, the subregions of the catalyst layer may be electrically decoupled from one another. Irrespective of this, it is also possible for the nanotubes of the array to be electrically decoupled from one another.

If the nanotube array has a plurality of subregions of the catalyst layer which are electrically decoupled from one another and/or a plurality of nanotubes which are electrically decoupled from one another, it is possible for a plurality of nanotubes to be used in parallel and independently of one another as components of an electric circuit (for example as electrical conductors) and/or as sensors.

According to the nanotube array of the invention, the nanotubes which are decoupled from one another are provided in planar form, i.e. they are arranged parallel to the surface plane of the substrate. They are preferably arranged parallel to and in each case at a distance from one another. This arrangement increases the mechanical stability of the nanotubes, since the latter are arranged in the horizontal direction, with the result that bending of the sensitive nanotubes is obviously avoided. By contrast, according to the prior art nanotubes project vertically out of a substrate surface and are therefore susceptible to mechanical disruption. The nanotube array of the invention is sufficiently mechanically robust to allow it to be used under laboratory conditions.

Furthermore, the nanotube array may have a circuit device by means of which the nanotubes can be driven and/or read individually. By way of example, the electrical resistance of each of the nanotubes can be recorded individually by means of the circuit device. The circuit device may be a conventional microelectronic circuit. In this way, a nanotube array is coupled to a conventional microelectronic circuit. The planar, horizontal arrangement of the nanotube is particularly suitable for integration in silicon microelectronics. In particular, the microelectronics may be provided as an integrated circuit in the substrate on which the at least one nanotube is also arranged.

Furthermore, at least one of the subregions of the catalyst layer may be at least partially surrounded by a further electrically insulating layer. In particular, the electrically insulating layer and the further electrically insulating layer between which the catalyst layer is arranged may project laterally beyond the catalyst layer, in order in this way to form a pore which can predetermine the direction of growth of the nanotube parallel to the surface of the substrate. The horizontal pore evidently serves as a template for the growth of the nanotube. The pore is formed by two walls which project beyond the catalyst layer on both sides and are formed by the electrically insulating layer and by the further electrically insulating layer. The first electrically insulating layer and the second electrically insulating layer cover a large part of the surface of the catalyst layer, and only a small surface region of the catalyst layer remains uncovered. This uncovered surface region is oriented perpendicular to the substrate surface. If a nanotube is allowed to grow on this surface of the catalyst layer, the direction of growth is predetermined by the geometry of the arrangement. The direction of growth of the carbon nanotube is perpendicular to the uncovered surface of the catalyst layer. Therefore, the direction of growth of the nanotube is horizontal, i.e. the nanotube grows in a direction which is parallel to the surface of the substrate. The first and second electrically insulating layers projecting beyond the catalyst layer on both sides mechanically guide the growth of the nanotube, with the result that the growth takes place in the horizontal direction parallel to the surface of the substrate. Since the direction of growth can be predetermined by the geometry of the pores, it is possible to achieve a defined structure of carbon nanotubes. This high degree of structural definition is advantageous when the nanotube array is being coupled to conventional silicon microelectronics.

A further advantage is that the nanotube array according to the invention provides individual nanotubes rather than tufts of nanotubes with diameters in the region of 50 nm, as in the prior art. The periodic provision of pores also makes it possible to achieve a periodic array of nanotubes. In this respect, it should be emphasized that the size of the pores can be selected to be sufficiently small for only a single nanotube to grow in or from a pore.

The electrically insulating layer and/or the further electrically insulating layer are preferably made independently from one another from one or a combination of the materials silicon nitride and silicon dioxide. Since these materials do not have a catalytic action for the growth of nanotubes, the choice of these materials ensures that each nanotube grows within a spatially accurately defined region in the interior of the pore, i.e. on the surface of the catalyst layer.

In the nanotube array of the invention, it is also possible for at least one of the subregions of the catalyst layer to be at least partially surrounded by a layer for preventing diffusion. Obviously, this layer for preventing diffusion which at least partially surrounds at least one of the subregions of the catalyst layer prevents catalyst material from diffusing into adjacent layers or material of the adjacent layers from diffusing into the catalyst layer. In particular, it is known that catalytically active metals tend to diffuse into silicon layers of, for example, a connected circuit. The layer for preventing diffusion increases the service life of the nanotube array and ensures that it remains able to function. The layer for preventing diffusion is preferably made from tantalum nitride material.

The catalyst layer is preferably made from one or a combination of the materials nickel, iron and cobalt. Alternatively, it is possible to use any other suitable material, in particular any other metal which catalyzes the growth of nanotubes.

It is preferable for the subregions of the catalyst layer to be arranged parallel to one another on the surface of the substrate. This parallel arrangement makes it possible to form pores which are arranged in parallel.

The nanotube array may be used as a gas sensor. For this intended application, it is necessary to have a nanotube with a substantially uncovered surface. Two electrodes are electrically coupled by means of the at last one nanotube. For the purposes of mechanical stabilization, the end sections of the at least one carbon nanotube may be arranged on a mechanically robust surface, for example an electrically insulating layer. The nanotube array described may be applied to a substrate, for example a silicon wafer. The resistance of the at least one nanotube between the two electrodes can be recorded by a means for recording the electrical resistance.

The use of the nanotube array as a gas sensor makes use of the above-described physical effect whereby the electrical resistance of nanotubes changes by approximately three orders of magnitude within a few seconds if a nanotube is exposed to a gas atmosphere, such as for example nitrogen oxide ($NO_2$) or ammonia ($NH_3$). It should be emphasized that the nanotube array of the invention which is used as a gas sensor is not restricted to the detection of the two gases mentioned, but rather can also be used to detect other gases, such as oxygen ($O_2$), whose presence leads to a change in the electrical resistance of the nanotubes. The nanotube array of the invention provides a sufficiently robust gas sensor which is also sufficiently selectively sensitive with respect to specific gases.

It should also be added that the two electrically conductive electrodes and the nanotubes may, for example, be integrated on a semiconductor chip, e.g. a CMOS chip. The means for recording the electrical resistance may, for example, be an ohmmeter.

The nanotubes in the nanotube array may be carbon nanotubes.

The steps of the method for producing a nanotube array are referred to by capital letters below for the sake of clarity.

In a step B of the method, a catalyst layer is applied to the surface of the layer arrangement, the catalyst layer having one or more subregions.

In a step F, at least one nanotube is grown on an uncovered part of the surface of a subregion of the catalyst layer, in such a manner that the at least one nanotube is arranged parallel to the surface of the layer arrangement.

Furthermore, in the method for producing a nanotube array, in a further step A, the layer arrangement mentioned in step B can be formed by applying an electrically insulating layer to a substrate.

Also, in a step C, a further electrically insulating layer can be applied to at least part of the surface of the layer arrangement, in such a manner that the further electrically insulating layer at least partially covers at least one of the subregions of the catalyst layer.

Furthermore, in a step D, a trench can be etched into a surface region of the layer arrangement.

In a step E, the catalyst layer can be partially etched back, in such a manner that the electrically insulating layer and the further electrically insulating layer project laterally beyond the catalyst layer, with the result that a pore as a guide for the growth of the nanotube is produced, predetermining the direction of growth of the nanotubes parallel to the surface of the substrate.

In a step F, at least one nanotube is grown on an uncovered part of the surface of a subregion of the catalyst layer, in such a manner that the at least one nanotube is arranged parallel to the surface of the layer arrangement.

According to a preferred configuration of the method according to the invention for producing a nanotube array, the abovementioned steps A to F are carried out in the following order:

First of all, in step A a layer arrangement is formed by applying an electrically insulating layer to a substrate. Then, in a subsequent step B, a catalyst layer is applied to the surface of the layer arrangement, the catalyst layer having one or more subregions. Then, in a further step C, a further electrically insulating layer is applied to at least part of the surface of the layer arrangement, in such a manner that the further electrically insulating layer partially covers at least one of the subregions of the catalyst layer. Then, in a step D, a trench is etched into a surface region of the layer arrangement. In a subsequent step E, the catalyst layer is partially etched back, in such a manner that the electrically insulating layer and the further electrically insulting layer project laterally beyond the catalyst layer, so that a pore which predetermines the direction of growth of the nanotube parallel to the surface of the substrate is produced. Then, in a step F, at least one nanotube is grown on an uncovered part of the surface of a subregion of the catalyst layer, in such a manner that the at least one nanotube is arranged parallel to the surface of the layer arrangement.

Evidently, in step A, an electrically insulating layer is formed on a substrate. This can be effected in particular by silicon nitride material being deposited on a silicon wafer. In step B, a catalyst layer is applied to the surface of the layer arrangement, the catalyst layer having one or more subregions. This can be implemented by a nickel layer which is suitable for use as a catalyst layer being deposited on the surface of the silicon nitride layer in a thickness of approximately 20 nm and this nickel layer being patterned to form wires which preferably run substantially parallel to one another and are approximately 20 nm wide using the electron beam lithography process. In the following step C, a further electrically insulating layer is applied to at least part of the surface of the layer arrangement, in such a manner that the further electrically insulating layer at least partially covers at least one of the subregions of the catalyst layer. For this purpose, by way of example, silicon dioxide material can be deposited on the surface of the layer arrangement and patterned by means of a photolithography method, so that the further electrically insulating layer remains only on part of the surface of the layer arrangement. In particular, the further electrically insulating layer at least partially covers the catalyst layer. In the further step D, a trench is etched into a surface region of the layer arrangement. This can be achieved by the uncovered region of the electrically insulating layer being partially etched back by means of a photolithography process. In a further step E, the catalyst layer is partially etched back, in such a manner that the electrically insulating layer and the further electrically insulating layer project beyond the catalyst layer on both sides, so that a pore which predetermines the direction of growth of the nanotube parallel to the surface of the substrate is produced. This method step can be implemented by etching back the nickel layer by wet-chemical means and in this way producing pores. These pores are evidently formed as a result of the nickel layer being etched back in a direction parallel to the substrate surface to such an extent that both the silicon nitride layer arranged beneath the nickel layer and the silicon dioxide layer arranged above the nickel layer project laterally beyond the nickel layer both above and below the latter. Then, in a step F, at least one nanotube is grown on an uncovered part of the surface of a subregion of the catalyst layer, in such a manner that the at least one nanotube is arranged parallel to the surface of the layer arrangement. The growth of the nanotubes can be effected, for example, using the vapor phase epitaxy process.

The method for producing a nanotube array has a number of advantages. Geometrically ordered structures of nanotubes in a planar arrangement can be produced by a combination of semiconductor technology nanostructuring techniques and a technique for growing nanotubes. As described above, the individual steps of the method are based on proven, standardized semiconductor technology processes. Therefore, there is no need to develop new installations for carrying out the method according to the invention for producing the nanotube array. This saves time and costs.

A major advantage of the method according to the invention consists in the fact that the pore geometry described above means that the production of nanotubes can be precisely predetermined with regard to dimensions and direction of growth. The cross-sectional area of a nanotube is fixed by the dimension of the uncovered catalyst surface, since the nanotube growth can only start from a catalytically active material. According to the invention, the preferred direction of growth of a nanotube is predetermined simply by the normal vector of the uncovered catalyst surface and is additionally stabilized by the electrically insulating layers arranged on both sides of the catalyst layer. This provides the nanotube with mechanical guidance during its growth, with the result that the nanotube grows in a predeterminable direction parallel to the surface of the substrate.

Furthermore, according to the invention the thickness of the catalyst layer can be set accurately. According to the example described above, the thickness of the catalyst layer is, for example, approximately 20 nm. As a result of a sufficiently low thickness being selected, it is ensured that only a single nanotube can grow on the pore.

According to another configuration of the method of the invention for producing a nanotube array, the sequence of the steps described individually above is altered compared to the exemplary embodiment described above. According to the exemplary embodiment described here, the step referred to above as D is carried out after step A and before step B. Specifically, the steps are carried out in the following order:

First of all, in step A, a layer arrangement is formed by applying an electrically insulating layer to a substrate. This step can be implemented by depositing a silicon nitride layer on a silicon wafer. In a subsequent step D, a trench is etched into a surface region of the layer arrangement. This can be achieved by photopatterning of the applied silicon nitride layer followed by etching. Then, in a step B, a catalyst layer is applied to the surface of the layer arrangement, the catalyst layer having one or more subregions. This can be implemented by a catalyst layer, for example a 20 nm thick nickel layer, being deposited on the surface of the layer arrangement and being patterned by means of electron beam lithography to form wires which run substantially parallel to one another and are approximately 20 nm thick. In a subsequent step C, a further electrically insulating layer is applied to at least part of the surface of the layer arrangement, in such a manner that the further electrically insulating layer at least partially covers at least one of the subregions of the catalyst layer. This method step can be implemented by firstly covering the surface of the layer structure with photoresist and then patterning the latter by means of a lithography process. Then, by way of example, a silicon nitride layer is deposited on the layer arrangement by sputtering or evaporation coating. Then, the silicon nitride layer and the photoresist layer below it can be removed from a subregion of the surface of the layer arrangement using a lift-off method. As a result, a silicon nitride layer remains only on a desired surface region of the layer arrangement, according to the invention only on the surface of the catalyst layer. Next, in a subsequent step E, the catalyst layer is partially etched back, in such a manner that the electrically insulating layer and the further electrically insulating layer project laterally beyond the catalyst layer, so that a pore which predetermines the direction of growth of the nanotube parallel to the surface of the substrate is produced. As has already been described above, this can be achieved by wet-chemically etching back nickel, so that pores remain. Then, in a further method step F, at least one nanotube is grown on the uncovered part of the surface of a subregion of the catalyst layer, in such a manner that the at least one nanotube is arranged parallel to the surface of the layer arrangement. Nanotubes can be produced, for example, by vapor phase epitaxy.

Furthermore, the method according to the invention may at a suitable point include a further method step in which at least in part at least one layer for preventing diffusion is introduced between at least one subregion of the catalyst layer and the layers which adjoin the at least one subregion of the catalyst layer. When coupling the nanotube array to conventional silicon microelectronics, it is advantageous to surround the catalytically active metal with diffusion barriers, since the catalyst metal can thermally diffuse into silicon regions of a connected circuit. Tantalum nitride can be used as material for the layer for preventing diffusion.

The electrically insulating layer and/or the further electrically insulating layer may be made from one or a combination of the materials silicon nitride and silicon dioxide. However, it is also possible to use any other material suitable for this purpose.

The catalyst layer is preferably produced from one or a combination of the materials nickel, iron and cobalt. Alternatively, it is possible to use any other material which catalyzes the growth of nanotubes.

It should be noted that the at least one nanotube which is applied to the arrangement according to the method is preferably a carbon nanotube.

Exemplary embodiments of the invention are illustrated in the figures and are explained in more detail below.

BRIEF DESCRIPTION OF THE DRAWINGS

In the drawing:

FIG. 1A shows a plan view of a nanotube array in accordance with a first exemplary embodiment of the invention, FIG. 1B shows a cross section through a nanotube array on section line I-I' from FIG. 1A, in accordance with the first exemplary embodiment of the invention, FIG. 1C shows a plan view of a nanotube array in accordance with a second exemplary embodiment of the invention, FIG. 1D shows a cross section through a nanotube array on section line II-II' from FIG. 1C in accordance with the second exemplary embodiment of the invention, FIG. 1E shows a plan view of a nanotube array in accordance with a third exemplary embodiment of the invention, FIG. 1F shows a cross section through a nanotube array on section line III-III' from FIG. 1E in accordance with the third exemplary embodiment of the invention, FIG. 3A shows a plan view (left) and a cross section on section line IVa-IVa' (right) of a layer arrangement following a first method section in accordance with a preferred exemplary embodiment of the method according to the invention for producing a nanotube array, FIG. 3B shows a plan view and a cross section on section line IVb-IVb' of a layer arrangement following a second method section in accordance with a preferred exemplary embodiment of the method according to the invention for producing a nanotube array, FIG. 4C shows a plan view and a cross section on section line Vc-Vc' of a layer arrangement following a third method section in accordance with the further preferred exemplary embodiment of the method according to the invention for producing a nanotube array, FIG. 4D shows a plan view and a cross section on section line Vd-Vd' of a layer arrangement following a fourth method section in accordance with the further preferred exemplary embodiment of the method according to the invention for producing a nanotube array, FIG. 4E shows a plan view and a cross section on section line Ve-Ve' of a layer arrangement following a fifth method section in accordance with the further preferred exemplary embodiment of the method according to the invention for producing a nanotube array.

DETAILED DESCRIPTION OF THE INVENTION

Figure 2:
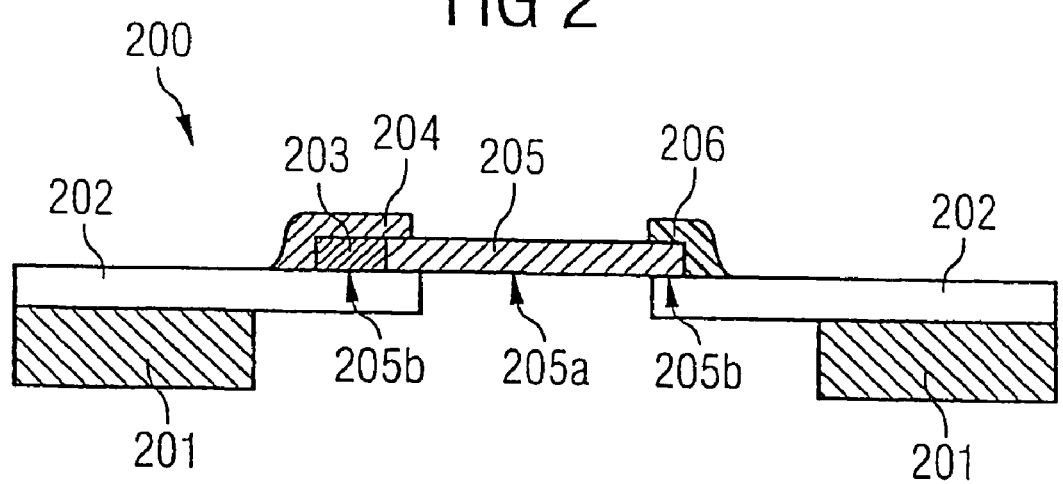
FIG. 2 shows a cross section through a nanotube array in accordance with an exemplary embodiment of the nanotube array according to the invention for use as a gas sensor.

FIG. 1A shows a first exemplary embodiment of a nanotube array 100 of the invention, which includes: a substrate 101, a catalyst layer 102, which has one or more subregions, on the surface of the substrate 101 and at least one nanotube 103 arranged on the surface of the catalyst layer 102, parallel to the surface of the substrate 101. In accordance with the exemplary embodiment shown in FIG. 1A, the nanotube array 100 has three subregions of the catalyst layer 102, in each case one nanotube 103 being arranged at each of the subregions of the catalyst layer 102. FIG. 1B shows a cross-sectional view on section line I-I' of the nanotube array 100 shown in FIG. 1A.

FIG. 1C shows a nanotube array 110 in accordance with a second exemplary embodiment of the invention. FIG. 1D shows a cross-sectional view on section line II-II' of the nanotube array 110 shown in FIG. 1C. Compared to the nanotube array 100, the nanotube array 110 additionally includes an electrically insulating layer 104 which is arranged between the substrate 101 and the catalyst layer 102. The electrically insulating layer 104 has a topography, i.e. a surface structure, which is such that the at least one nanotube 103 at its end sections 103a rests on the electrically insulating layer 104 and is clear in its center section 103b.

As can be seen in particular from the plan view of the nanotube array 110 shown in FIG. 1C, the subregions of the catalyst layer 102 are electrically decoupled from one another. The subregions of the nanotubes 103 are also electrically decoupled from one another.

FIG. 1E shows a plan view of a nanotube tube array 120 as a third exemplary embodiment of the invention. FIG. 1F shows a cross-sectional view on section line III-III' of the nanotube array 120 shown in FIG. 1E. The nanotube array 120, in addition to the features shown in the nanotube arrays 100, 110, also includes additional features: the nanotube array 120 shown in FIG. 1E, FIG. 1F has a circuit device 105, by means of which the nanotubes 103 can be driven and/or read individually. Furthermore, in accordance with the nanotube array 120 shown in FIG. 1E, FIG. 1F, all three subregions of the catalyst layer 102 are surrounded by a further electrically insulating layer 106. The fact that the electrically insulating layer 104 and the further electrically insulating layer 106, between which the catalyst layer 102 is arranged, project laterally beyond the catalyst layer 102 on both sides results in the formation of a pore which can be used to predetermine the direction of growth of the nanotubes 103 parallel to the surface of the substrate 101. Furthermore, as shown in FIG. 1F, at least one of the subregions of the catalyst layer 102 is surrounded by a layer for preventing diffusion 107.

The nanotube array 120 can be coupled to external electronics, for example a CMOS circuit, by means of the circuit device 105. As indicated in FIG. 1E, each of the three nanotubes 103 is coupled to a connection electrode 108 of the circuit device 105 via the electrically conductive catalyst layer 102.

If three horizontal pores, each of which serves as a template for the growth of one of the three nanotubes 103, have been produced by the geometric arrangement of the electrically insulating layer 104, of the three subregions of the catalyst layer 102 and of the further electrically insulating layer 106 which can be seen from FIG. 1F, the result is a planar arrangement of nanotubes 103. By precisely predetermining the location of growth and direction of growth, it is possible to produce arrays of nanotubes which can be structured geometrically accurately.

The electrically insulating layer 104 and/or the further electrically insulating layer 106 are made from one or a combination of the materials silicon nitride and silicon dioxide. According to alternative exemplary embodiments of the invention, the electrically insulating layer 104 and/or the further electrically insulating layer 106 may be made from another suitable material which must have the property of having no catalytic action with regard to the growth of nanotubes 103. The nanotube array 120 includes a layer for preventing diffusion 107, which is preferably made from tantalum nitride. This prevents material of the catalyst layer from diffusing into any adjoining silicon regions of a coupled microelectronic circuit, for example under thermal influences. Therefore, the layer for preventing diffusion 107 acts as a diffusion barrier for the catalytically active material.

According to this exemplary embodiment, the catalyst layer 102 is made from one or a combination of the materials nickel, iron and cobalt. However, it is also possible to use any other suitable material which catalyzes the growth of nanotubes 103. If, as symbolically indicated in FIG. 1E and FIG. 1F, the nanotubes 103 are to be coupled to connection electrodes 108 of an external circuit device 105 by means of the catalyst layer 102, an electrically conductive material is to be selected for the catalyst layer 102.

The nanotubes 103 in the nanotube arrays 100, 110, 120 are carbon nanotubes.

FIG. 2 shows a gas sensor 200 as an example of an application for the nanotube array according to the invention. The gas sensor 200 has a patterned substrate 201, an electrically insulating layer 202, an electrically conductive catalyst layer 203, a further electrically insulating layer 204, a carbon nanotube 205 and an electrode 206.

The functionality of the gas sensor 200 is based on the physical effect described above whereby the electrical resistance of a carbon nanotube 205 is extremely sensitively dependent on the gas atmosphere surrounding the carbon nanotube 205. As described above, in an ammonia atmosphere ($NH_3$), the electrical conductivity of carbon nanotubes is reduced by approximately three powers of ten. Conversely, the electrical conductivity increases by approximately three orders of magnitude if the carbon nanotube 205 is exposed to a nitrogen dioxide ($NO_2$) atmosphere in a concentration of 200 ppm (parts per million, $10^{-6}$).

If the electrical resistance of the carbon nanotube 205 between the electrically conductive layers 203 and 206 is taken in a means for recording the electrical resistance (not shown in FIG. 2) when the surface of the carbon nanotube 205 which is clear in its central section 205a is exposed to a specific gas atmosphere, the value of the electrical resistance of the carbon nanotube 205 is a characteristic measure of the type or concentration of the gas which surrounds the carbon nanotube 205. The means for recording the electrical resistance is preferably integrated in the substrate. The carbon nanotube 205 arranged between the electrically conductive catalyst layer 203 and the electrically conductive electrode 206 is preferably to be provided with a surface which is substantially uncovered in its central section 205a. By contrast, the end sections 205b of the nanotube 205 are not uncovered, but rather are coupled to the further electrically insulating layer 204 or to the electrically conductive electrode 206.

To increase the measurement accuracy of the gas sensor 200, it is possible for a plurality of carbon nanotubes 205, all or some of which are exposed to a specific gas atmosphere, to be connected either in parallel or in series or partly in parallel and partly in series. Referring to FIG. 2, this can be achieved, for example, by the individual carbon nanotubes 205 being arranged substantially parallel to one another in a plane perpendicular to the plane of the drawing.

The gas sensor 200 shown in FIG. 2 may, for example, be operated as described below. The arrangement 200 is brought into operative contact with a gas atmosphere which is to be detected. The means for recording the electrical resistance can be used to determine the electrical resistance of the carbon nanotube 205 between the electrically conductive contacts 203, 206 of the carbon nanotube 205, the value of the electrical resistance of the carbon nanotube 205 being characteristic of the concentration or nature of the surrounding gas. As a result of the sensitive carbon nanotube 205 being applied to the robust electrically insulating layer 202 or to the robust patterned substrate 201, the gas sensor 200 is made sufficiently robust to be suitable for practical use in a laboratory.

The following text, referring to FIG. 3A, FIG. 3B, FIG. 3C, FIG. 3D, FIG. 3E, FIG. 3F and FIG. 3G describes a first preferred exemplary embodiment of the method according to the invention for producing a nanotube array which includes the method steps A, B, C, D, E, F. In accordance with the exemplary embodiment described, these steps are to be carried out in the order A, B, C, D, E, F. The left-hand side of FIG. 3A, FIG. 3B, FIG. 3C, FIG. 3D, FIG. 3E, FIG. 3F and FIG. 3G in each case shows a plan view of the layer arrangement which is in each case obtained after the individual method steps have been carried out, while the right-hand side in each case shows an associated cross-sectional view on section lines IVa-IVa', IVb-IVb', IVc-IVc', IVd-IVd', IVe-IVe', IVf-IVf' and IVg-IVg' of this layer arrangement.

In step A, a layer arrangement 300 is formed by applying an electrically insulating layer 301 to a substrate 302.

The layer structure 300 obtained after step A has been carried out is shown in FIG. 3A. The substrate 302 is preferably a silicon wafer; alternatively, the substrate 302 may also be a glass substrate. By way of example, the electrically insulating layer 301 deposited on the substrate 302 may be a silicon nitride layer or may alternatively be a silicon dioxide layer.

In step B, a catalyst layer 303 is applied to the surface of the layer arrangement 300, the catalyst layer 303 having one or more subregions.

After step B has been carried out, a layer arrangement 304 is obtained (cf. FIG. 3B). In accordance with the layer arrangement 304 shown in FIG. 3B, the catalyst layer 303 has five subregions. Step B is implemented by, in a first substep, depositing a catalyst layer 303 on the surface of the layer arrangement 300. A 20 nm thick nickel layer is deposited on the surface of the layer structure 300. This nickel layer which has been deposited over the entire surface of the layer structure 300 is then patterned in a second substep using a suitable lithography process, for example by means of electron beam lithography. It is preferable for the nickel layer which has been deposited to be patterned in such a manner that wires with a diameter of 20 nm remain.

Then, in a step C, a further electrically insulating layer 305 is applied to at least part of the surface of the layer arrangement 304, in such a manner that the further electrically insulating layer 305 at least partially covers at least one of the subregions of the catalyst layer 303.

Figure 3C:
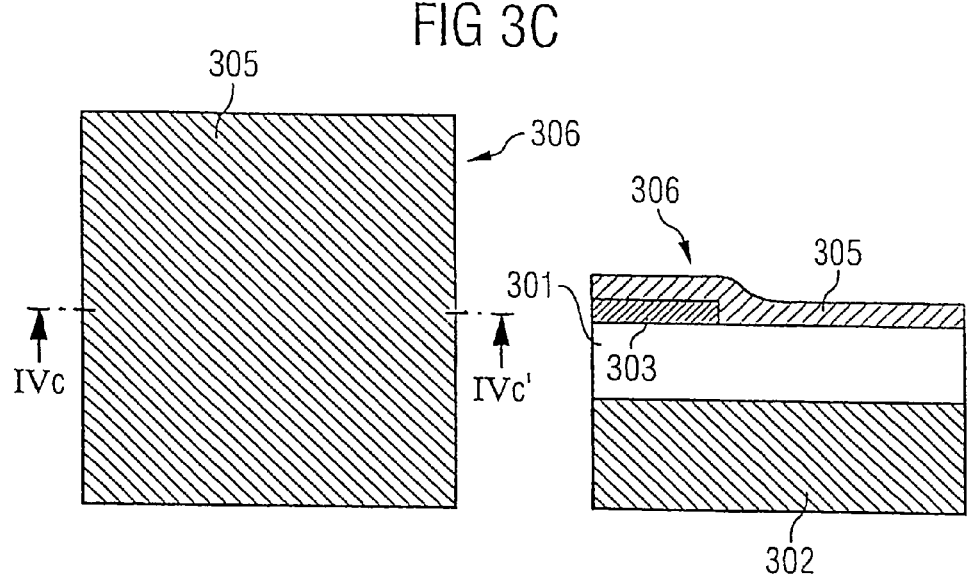
FIG. 3C shows a plan view and a cross section on section line IVc-IVc' of a layer arrangement following a third method section in accordance with a preferred exemplary embodiment of the method according to the invention for producing a nanotube array.
Figure 3D:
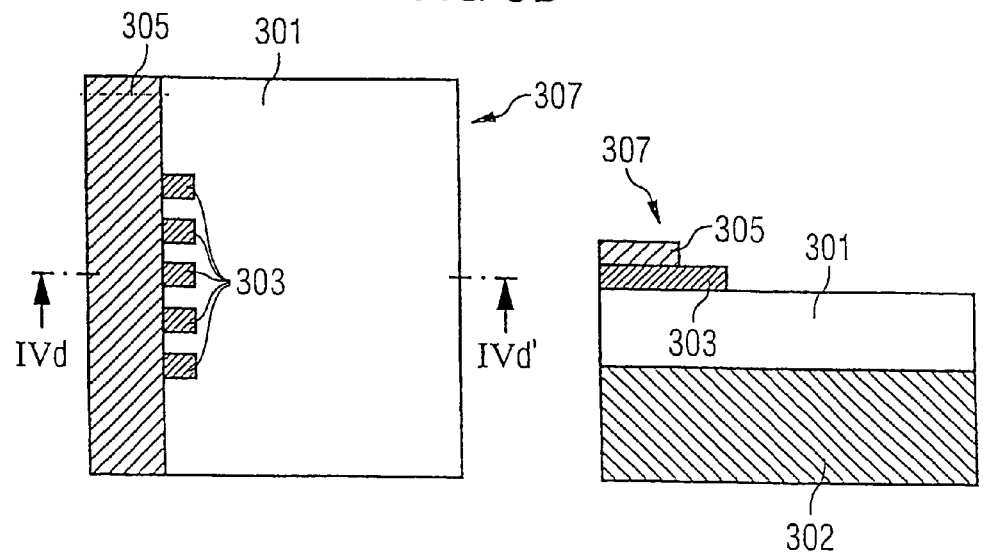
FIG. 3D shows a plan view and a cross section on section line IVd-IVd' of a layer arrangement following a fourth method section in accordance with a preferred exemplary embodiment of the method according to the invention for producing a nanotube array.

The substeps of step C can be understood with reference to FIG. 3C and FIG. 3D. In a first substep, the further electrically insulating layer 305 is applied to the surface of the layer arrangement 304. This can be achieved, for example, by a silicon dioxide layer being applied to the surface of the layer arrangement 304. This results in a layer arrangement 306 as shown in FIG. 3C. Then, in a second substep, the further electrically insulating layer 305 which has been applied is patterned using a suitable lithography or etching process. This results in the layer arrangement 307 shown in FIG. 3D, in which a subregion of the further electrically insulating layer 305 partially covers the catalyst layer 303.

In a subsequent step D, a trench 308 is etched into a surface region of the layer arrangement 307.

Figure 3E:
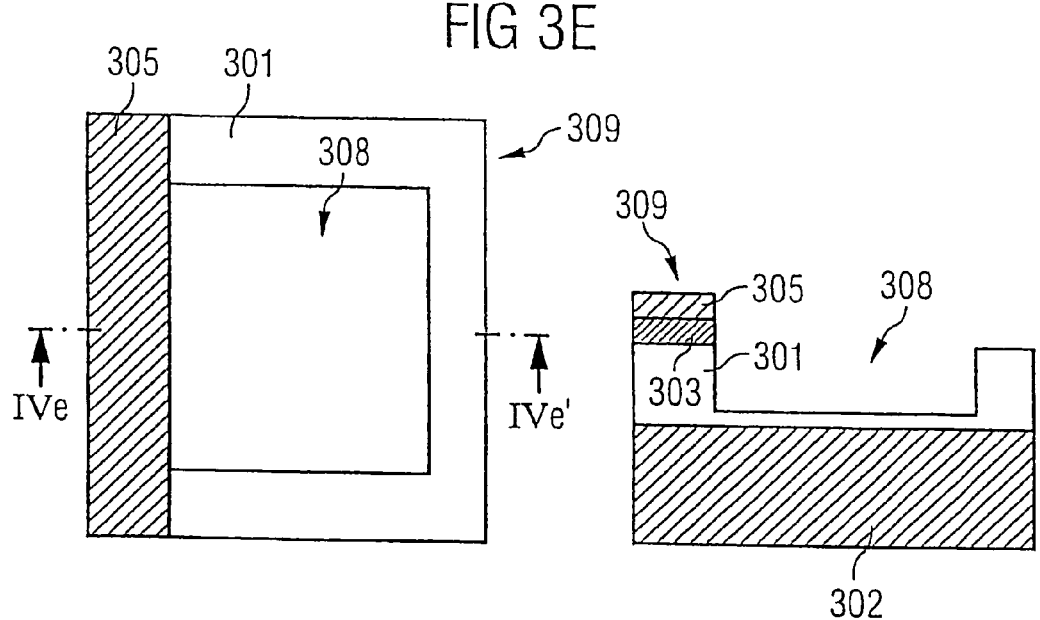
FIG. 3E shows a plan view and a cross section on section line IVe-IVe' of a layer arrangement following a fifth method section in accordance with a preferred exemplary embodiment of the method according to the invention for producing a nanotube array.

This results in the layer arrangement 309 illustrated in FIG. 3E. Method step D is implemented by means of a suitable photolithography process.

In a next method step E, the catalyst layer 303 is partially etched back, in such a manner that the electrically insulating layer 301 and the further electrically insulating layer 305 project laterally beyond the catalyst layer 303, so that a pore 310 which predetermines the direction of growth of the nanotube parallel to the surface of the substrate 302 is produced.

Figure 3F:
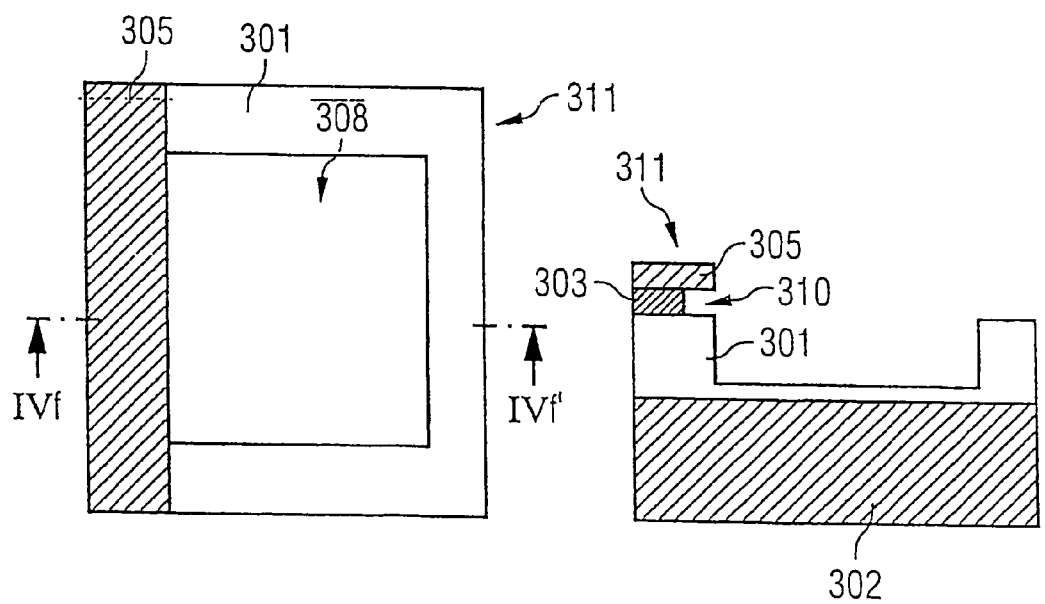
FIG. 3F shows a plan view and a cross section on section line IVf-IVf' of a layer arrangement following a sixth method section in accordance with a preferred exemplary embodiment of the method according to the invention for producing a nanotube array.

After this method step, the layer arrangement 311 illustrated in FIG. 3F is obtained. The formation of a pore 310 as a result of the electrically insulating layer 301 and the further electrically insulating layer 305 projecting laterally beyond the catalyst layer 303 on both sides substantially defines the way in which the subsequent growth of the nanotube takes place (cf. step F, below). Since nanotubes preferentially grow on catalytically active material, i.e. on uncovered surface regions of the catalyst layer 303, the "seed point" for the nanotube growth is defined. Furthermore, the direction of growth is defined as a result of the electrically insulating layer 301 and the further electrically insulating layer 305 projecting beyond the catalyst layer 303. A guide or template for the growth of the nanotube is obviously provided. As a result, it is possible to use the pore geometry to control the diameter, direction of growth and arrangement of the nanotubes. In process engineering terms, the catalyst layer 303 can be etched back by means of wet-chemical etchback methods. For example, the prior art has disclosed methods which allow catalyst layers 303 consisting, for example, of nickel to be etched back by wet-chemical means.

In a subsequent step F, at least one nanotube 312 is grown on an uncovered part of the surface of a subregion of the catalyst layer 303, in such a manner that the at least one nanotube 312 is arranged parallel to the surface of the layer arrangement 311.

Figure 3G:
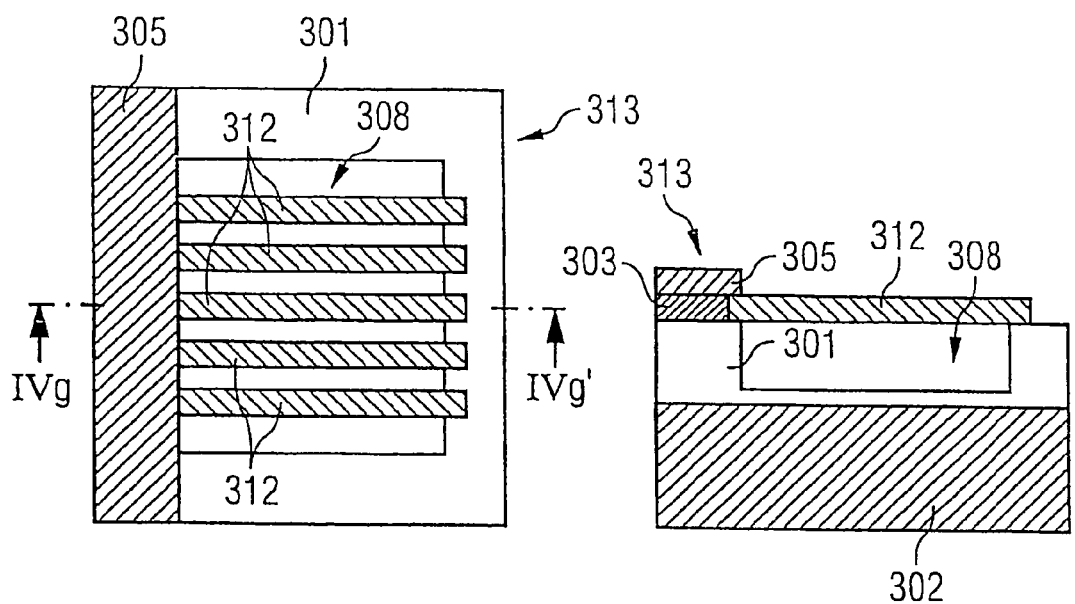
FIG. 3G shows a plan view and a cross section on section line IVg-IVg' of a layer arrangement following a seventh method section in accordance with a preferred exemplary embodiment of the method according to the invention for producing a nanotube array.

After step F has been carried out, the layer arrangement 313 which is illustrated in FIG. 3G is obtained. The nanotubes 312 are produced, for example, by means of vapor phase epitaxy. As stated above, the direction of growth and diameter of the nanotubes 312 can be predetermined by the pores 310 and by the thickness of the catalyst layer 303.

The text which follows explains a second exemplary embodiment of the method according to the invention for producing a nanotube array with reference to FIG. 4A, FIG. 4B, FIG. 4C, FIG. 4D, FIG. 4E. This exemplary embodiment differs from the exemplary embodiment explained above substantially with regard to the order in which steps A to F are carried out. The left-hand side of FIG. 4A, FIG. 4B, FIG. 4C, FIG. 4D and FIG. 4E in each case shows a plan view of the layer arrangement obtained after each of the individual method steps have been carried out, while the right-hand side in each case shows an associated cross-sectional view on section lines Va-Va', Vb-Vb', Vc-Vc', Vd-Vd' and Ve-Ve' of this layer arrangement.

The second exemplary embodiment of the method according to the invention for producing a nanotube array includes the following steps:

In step A, a layer arrangement 400 is formed as a result of an electrically insulating layer 401 being applied to a substrate 402.

Figure 4A:
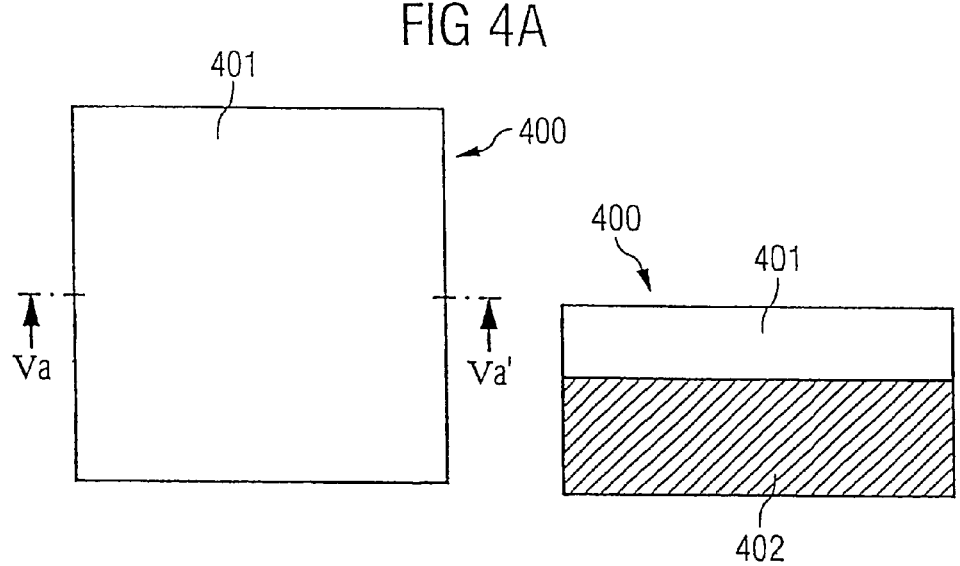
FIG. 4A shows a plan view (left) and a cross section on section line Va-Va' (right) of a layer arrangement following a first method section in accordance with a further preferred exemplary embodiment of the method according to the invention for producing a nanotube array.

The layer structure 400 shown in FIG. 4A is obtained after step A. The electrically insulating layer 401 is a silicon nitride layer or alternatively a silicon dioxide layer, and the substrate 402 is a silicon wafer or alternatively a glass substrate.

In a step D which follows step A, a trench 403 is etched into a surface region of the layer arrangement 400.

Figure 4B:
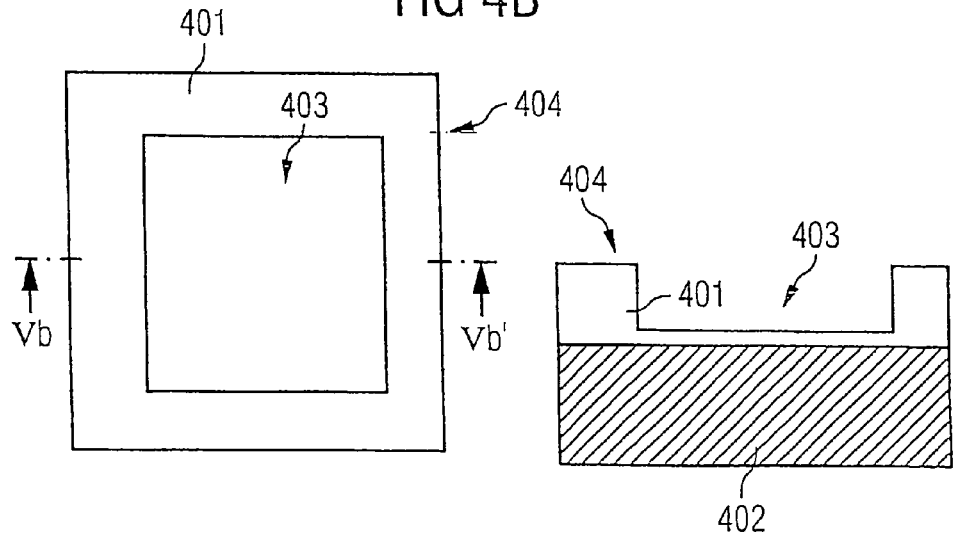
FIG. 4B shows a plan view and a cross section on section line Vb-Vb' of a layer arrangement following a second method section in accordance with the further preferred exemplary embodiment of the method according to the invention for producing a nanotube array.

The introduction of the trench 403 into the electrically insulating layer 401 on the surface of the substrate 402 is achieved by photopatterning and subsequent etching of the surface of the layer structure 400. After step D, which follows step A, has been carried out, the layer arrangement 404 shown in FIG. 4B is obtained.

In a step B which follows step D described above, a catalyst layer 405 is applied to the surface of the layer arrangement 404, the catalyst layer 405 having one or more subregions.

In accordance with the layer arrangement 406 illustrated in FIG. 4C, which is obtained after step B has been carried out, the catalyst layer 405 has five subregions. In practical implementation, the method step referred to as step B usually comprises a plurality of substeps. In a first substep, a catalyst layer 405 is applied to the entire surface of the layer structure 404. By way of example, a layer of nickel which is approximately 20 nm thick is deposited over the surface of the layer structure 404. In a second substep of step B, the catalyst layer 405 is patterned by means of a suitable lithography process, for example by means of electron beam lithography, in such a manner that one or more subregions remain on the surface of the layer arrangement 404. Referring to FIG. 4C, after this substep five subregions of the catalyst layer 405 remain on the surface of the layer structure. It is preferable for the catalyst layer 405 to be patterned to form wires of a width of approximately 20 nm. As shown in the cross-sectional view presented in FIG. 4C, after the photopatterning material of the catalyst layer 405 remains on the surface of the layer structure 406 only in a region arranged to the left of the trench 403.

In a subsequent step C, a further electrically insulating layer 407 is applied to at least part of the surface of the layer arrangement 406, in such a manner that the further electrically insulating layer 407 at least partially covers at least one of the subregions of the catalyst layer 405.

The method step referred to as step C also includes a plurality of substeps. In a first substep, a photoresist layer is deposited on the surface of the layer structure 406. In a second substep, a lithography process with a suitable mask is used to pattern the surface of the layer arrangement 406 covered by the photoresist. In a further substep, a further electrically insulating layer 407, for example comprising silicon nitride material or silicon dioxide material, is deposited on the surface of the layer arrangement 406, which has been provided with photoresist and photopatterned, by means of a suitable semiconductor technology process, for example by sputtering or evaporation coating. In a further substep, the double layer composed of the photoresist layer and the electrically insulating layer 407 is removed from a subregion of the surface of the layer arrangement using a lift-off method. What remains is a layer arrangement which differs from the layer arrangement 406 illustrated in FIG. 4C substantially through the fact that the further electrically insulating layer 407 remains in place in a surface region of the layer arrangement which in accordance with the cross-sectional view of the layer arrangement is located to the left of the left-hand boundary of the trench 403.

In a subsequent method step E, the catalyst layer 405 is partially etched back, in such a manner that the electrically insulating layer 401 and the further electrically insulating layer 407 project laterally beyond the catalyst layer 405, so that a pore 408 which predetermines the direction of growth of the nanotube parallel to the surface of the substrate 402 is produced.

After method step E has been carried out, the layer arrangement 409 shown in FIG. 4D is obtained. Step E can be implemented by etching back the catalyst layer 405 by wet-chemical means and in this way forming pores 408. By way of example, a catalyst layer 405 made from nickel is etched back by means of a wet-chemical etching process. As described above, the formation of pores 408 for defining the direction of growth of a nanotube, the diameter of a nanotube and the production of an ordered structure of nanotubes is essential.

In a subsequent method step F, at least one nanotube 410 is grown on an uncovered part of the surface of a subregion of the catalyst layer 405, in such a manner that the at least one nanotube 410 is arranged parallel to the surface of the layer arrangement 409.

After the method step F has been carried out, the layer arrangement 411 shown in FIG. 4E is obtained. Nanotubes 410 can be produced, for example, by means of the vapor phase epitaxy process, which is known from the prior art.

Furthermore, the described method for producing a nanotube array may include the further step of introducing a layer for preventing diffusion (not shown in the figures) between at least one subregion of the catalyst layer 405 and the adjoining layers 401, 407. This makes it possible to prevent the material of the catalyst layer 405 from diffusing into regions of any connected external circuit (not shown in the figures), for example as a result of thermal influences. The layer for preventing diffusion (provided with reference numeral 107 in FIG. 1F) is preferably made from tantalum nitride.

The electrically insulating layer 401 and/or the further electrically insulating layer 407 are produced independently from one another from one or a combination of the materials silicon nitride and silicon dioxide.

The catalyst layer 405 is preferably made from one or a combination of the materials nickel, iron and cobalt. Alternatively, any other catalytically active material can be used to produce the catalyst layer 405.

According to the present exemplary embodiment, the nanotubes 410 which are to be grown onto the layer arrangement 409 are carbon nanotubes.

The text which follows describes a further exemplary embodiment of the method according to the invention for producing a nanotube array which is tailored to the use of the nanotube array which has been produced using the method as a gas sensor.

The method described below for the production of the gas sensor is described with reference to FIG. 5A, FIG. 5B, FIG. 5C, FIG. 5D.

In a first step A, a layer arrangement 504 is formed by applying an electrically insulating layer 501, 502 to a substrate 503.

Figure 5A:
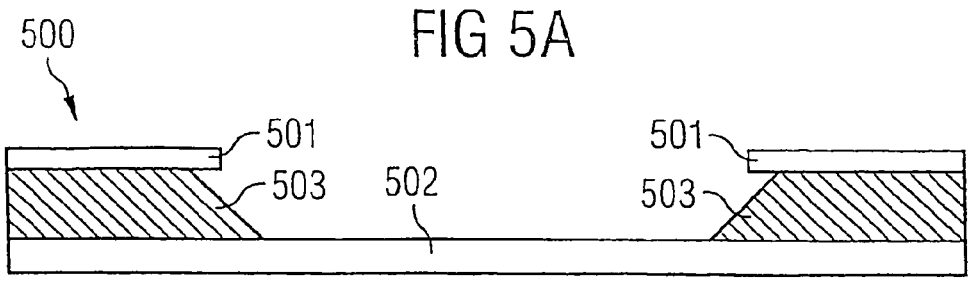
FIG. 5A shows a cross section through a layer arrangement following a first method section in accordance with a third preferred exemplary embodiment of the method according to the invention for producing a nanotube array.
Figure 5B:
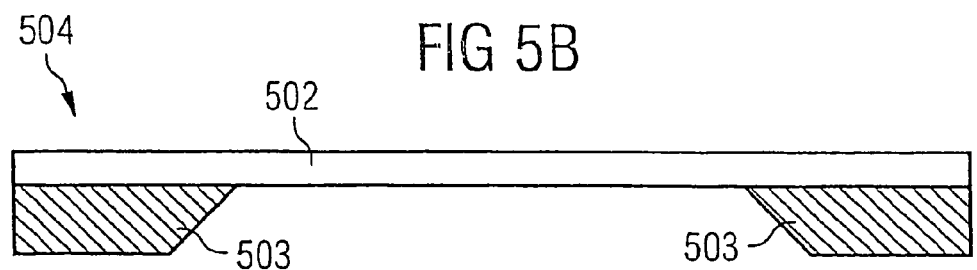
FIG. 5B shows a cross section through a layer arrangement following a second method section in accordance with the third preferred exemplary embodiment of the method according to the invention for producing a nanotube array.

After step A has been carried out, the layer arrangement 504 illustrated in FIG. 5B is obtained. Step A includes a plurality of substeps. In a first substep, an electrically insulating layer is applied to both main sides of a substrate 503. In FIG. 5A, these two layers are referred to as first electrically insulating layer 501 and second electrically insulating layer 502. The substrate 503 is preferably a silicon wafer, and the first electrically insulating layer 501 and/or the second electrically insulating layer 502 are preferably made from silicon nitride material or alternatively from silicon dioxide material. It is also possible for the first insulating layer 501 and the second electrically insulating layer 502 to be made from different materials. To pattern the substrate 502, in a next substep first of all the electrically insulating layer 501 which has been applied to a main side of the substrate 503 is patterned by means of a suitable semiconductor technology process in such a manner that a surface region of the substrate 503 is uncovered in a central region of the layer arrangement 500. Evidently, a hole, for example a substantially circular or rectangular hole, is etched into the first electrically insulating layer 501. In a following substep, a suitable etching process is applied to the layer structure in order to remove the material of the substrate 503 from the central region of the arrangement, in which part of the surface of the substrate has previously been uncovered by the etching process. To do this, an etching process in which the etching chemicals used are to be selected in such a way that they etch the material of the substrate 503 whereas the materials of the first electrically insulating layer 501 and of the second electrically insulating layer 502 are not attacked by the etching chemical is to be used. After the substeps described have been carried out, the layer arrangement 500 shown in FIG. 5A is obtained. In a following substep, the first electrically insulating layer 501 is removed from the surface of the layer structure 500, resulting in the layer structure 504 shown in FIG. 5B. This can be achieved, for example, by means of a suitable etching process.

The method steps described below are carried out predominantly on that main side of the second electrically insulating layer 502 which is remote from the substrate 503. To make this clearer in the drawings, in FIG. 5B the layer arrangement 504 has been rotated through an angle of 180° with respect to the layer arrangement 500 shown in FIG. 5A.

In a step B, a catalyst layer 505 is applied to the surface of the layer arrangement 504, the catalyst layer 505 having one or more subregions.

The layer structure obtained after step B has been carried out is not shown in the figures. Method step B is implemented by first of all applying a catalyst layer 505 which completely covers the surface of the layer structure 504 and then patterning this catalyst layer 505 by means of a suitable semiconductor technology process, for example by means of the electron beam lithography process. By way of example, an iron layer, a cobalt layer or a nickel layer or a layer of any other material which catalyzes the growth of nanotubes can be applied and can be patterned to form wires with a thickness of, for example, 20 nm using the electron beam lithography process. The individual subregions of the catalyst layer 505 cannot be seen from the cross-sectional views of the FIG. 5C, FIG. 5D.

In a subsequent method step C, a further electrically insulating layer 506 is applied to at least part of the surface of the layer arrangement, in such a manner that the further electrically insulating layer 506 at least partially covers at least one of the subregions of the catalyst layer 505.

Method step C is implemented by first of all applying a further electrically insulating layer 506 which covers the entire surface of the layer arrangement and patterning this layer by means of a suitable semiconductor technology process. By way of example, the further electrically insulating layer 506 is a silicon dioxide layer, or, alternatively, the further electrically insulating layer 506 may be a silicon nitride layer which is then patterned, for example, by means of a photolithography method.

In the next method step D, a trench 507 is etched into a surface region of the layer arrangement.

In practice, this step is implemented by patterning the surface of the layer arrangement, for example using a photolithography process.

In a method step E, the catalyst layer 505 is partially etched back, in such a manner that the electrically insulating layer 502 and the further electrically insulating layer 506 project laterally beyond the catalyst layer 505, so that a pore 508 which predetermines the direction of growth of the nanotubes parallel to the surface of the substrate 503 is produced.

Figure 5C:
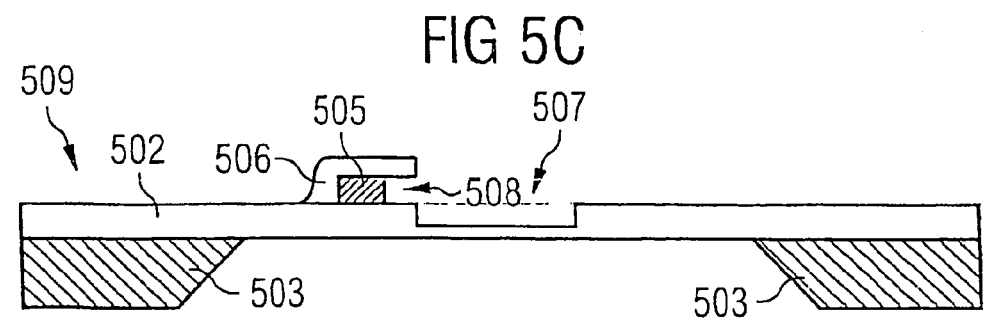
FIG. 5C shows a cross section through a layer arrangement following a third method section in accordance with the third preferred exemplary embodiment of the method according to the invention for producing a nanotube array.

This results in the layer structure 509 shown in FIG. 5C. The method step E can be implemented by etching back the catalyst layer 505 by wet-chemical means in order in this way to produce a pore 508.

Figure 5D:
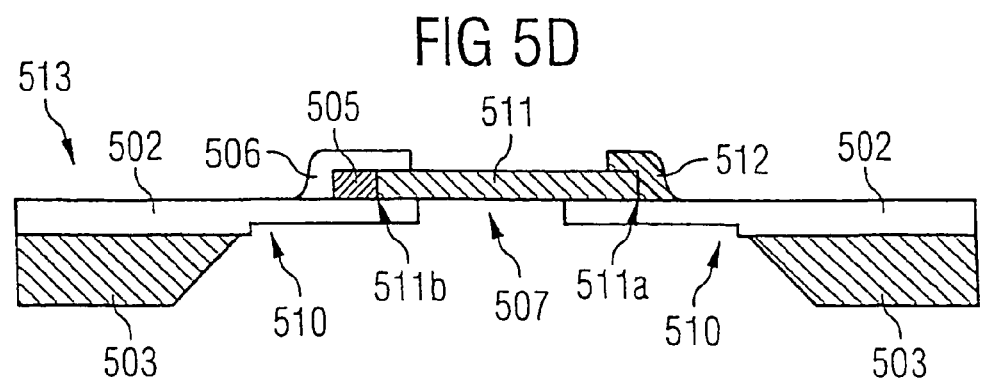
FIG. 5D shows a cross section through a layer arrangement following a fourth method section in accordance with the third preferred exemplary embodiment of the method according to the invention for producing a nanotube array.

To enable the nanotube array which has been produced using the method to be used as a gas sensor (for which use the maximum possible part of the surface of the nanotube should be uncovered), the exemplary embodiment of the production method according to the invention described includes a few particular features. Since the nanotube which is to be applied in a further method step must come into operative contact with a surrounding gas atmosphere, so that as a result of the operative contact the electrical resistance of the nanotube changes in a manner which is characteristic of the surrounding gas, in the gas sensor produced the at least one nanotube must be uncovered, i.e. exposed to the surrounding gas, in the largest possible surface region. To achieve this, in an intermediate method step E1, the second electrically insulating layer 502 is partially etched back in a central region on its main side of the second electrically insulating layer which faces the substrate 503. This results in the formation of the groove 510 which is illustrated in FIG. 5D and is introduced into the second electrically insulating layer 502 to a sufficient depth to produce a through-hole through the second electrically insulating layer 502 together with the trench 507.

Then, in a subsequent method step F, at least one nanotube 511 is grown on an uncovered part of the surface of a subregion of the catalyst layer 505, in such a manner that the at least one nanotube 511 is arranged parallel to the surface of the layer arrangement.

The nanotubes 511 are produced, for example, by using the vapor phase epitaxy process. A pore 508 is formed on account of the second electrically insulating layer 502 (from below in accordance with FIG. 5D) and the further electrically insulating layer 506 (from above in accordance with FIG. 5D) projecting laterally beyond the catalyst layer 505 on both sides. The nanotubes 511 can only start to grow from the surface of a catalytically active layer. Therefore, the at least one nanotube 511 can only grow out of the pore 508, starting from the uncovered surface of the catalyst layer 505. Since the direction of growth can be predetermined by the channel-like template which is formed by the second electrically insulating layer 502 and the further electrically insulating layer 506, it is possible to define the direction of growth of the nanotube 511. Therefore, the invention makes it possible to ensure that the nanotube 511 shown in FIG. 5D can only grow in the horizontal direction, i.e. in a direction parallel to the surface of the substrate 503. The diameter of the nanotube 511 can be predetermined by the thickness of the catalyst layer 505. As a result, individual nanotubes 511 can be grown by suitably selecting the thickness of the catalyst layer 505.

For the nanotube array of the invention to be used as a gas sensor, it is necessary to carry out a further additional step, since the use of the nanotube array as a gas sensor requires a physical variable of the nanotube which is sensitive to a surrounding gas atmosphere to be recorded. As described above, in particular the electrical resistance of a nanotube is a variable which is sensitive to the nature and concentration of a surrounding gas. Therefore, the electrical resistance of the nanotube 511 has to be recorded, and for this purpose the nanotube array which is to be used as a gas sensor is to be coupled to a means for recording the electrical resistance (not shown in the figures). For this purpose, electrical contact has to be made with the at least one nanotube 511 on both sides, so that it can be coupled to the means for recording the electrical resistance via these two electric contacts. Therefore, in a further additional step, it is necessary to make electric contact with the uncovered end section 511a of the nanotube 511 which is not coupled to the catalyst layer 505. For this purpose, an electrically conductive electrical contact 512 is applied to the layer structure in order to be coupled to the uncovered end section 511a of the nanotube 511. The resulting layer structure 513 is shown in FIG. 5D. FIG. 5D does not show the electrical contact made with the other end section 511b of the nanotube 511, which is coupled to the catalyst layer 505. Electric contact has to be made with this other end section 511b of the nanotube 511 which is coupled to the catalyst layer 505 too in order for it to be possible to record the electrical resistance of the nanotube 511 between the two end sections 511a, 511b of the nanotube 511.

After these method steps have been carried out, the layer structure 513 shown in FIG. 5D, which can be used as a gas sensor, is obtained. It should be emphasized that the use of the nanotube array of the invention as a gas sensor is not restricted to the exemplary embodiment shown in FIG. 5D. For example, it is possible for a plurality of nanotubes 511 to be electrically connected in series, in order to increase the overall resistance to be recorded and in this way to increase the sensitivity of the gas sensor arrangement. Alternatively, it is also possible for a plurality of nanotubes 511 to be connected in parallel, in order for their electrical resistance to be recorded separately for each nanotube and in this way to increase the detection accuracy by means of multiple measurement. It is also possible for some of the nanotubes 511 to be connected in parallel and for others of the nanotubes 511 to be connected in series. Furthermore, the way in which the nanotube array functions as a gas sensor is not restricted to the electrical resistance of the nanotube 511 being recorded. It is also possible for any other physical parameter of the nanotube 511 which is sensitive to a physical variable which is to be recorded to be measured by means other than electrical.

The invention claimed is:

1. A gas sensor having a nanotube array, comprising:
   a substrate;
   a catalyst layer, which includes more than one subregion, on the surface of the substrate;
   at least one nanotube arranged on the surface of the catalyst layer, parallel to the surface of the substrate;
   a pore, the pore being used to predetermine the direction of growth of the nanotube starting from the catalyst layer and parallel to the surface of the substrate; and an electrically insulating layer between the substrate and the catalyst layer, wherein the electrically insulating layer has a topography which is such that the at least one nanotube rests on the electrically insulating layer at its end sections and is free in its central section wherein the substrate is a patterned substrate such that at least part of the substrate below the central section of the at least one nanotube is removed.

2. The nanotube array as claimed in claim 1, further comprising an electrically insulating layer between the substrate and the catalyst layer.

3. The nanotube array as claimed in claim 2, further comprising the electrically insulating layer having a topography which is such that the at least one nanotube rests on the electrically insulating layer at its end sections and is free in its central section.

4. The nanotube array as claimed in one of claims 1 to 3, in which the subregions of the catalyst layer are decoupled from one another and/or in which the nanotubes are decoupled from one another.

5. The nanotube array as claimed in one of claims 1 to 3, further comprising a circuit device, by means of which the nanotubes can be driven and/or read individually.

6. The nanotube array as claimed in one of claims 1 to 3, further comprising, at least one of the subregions of the catalyst layer is at least partially surrounded by a further electrically insulating layer.

7. The nanotube array as claimed in claim 6, in which the electrically insulating layer and the further electrically insulating layer, between which the catalyst layer is arranged, project laterally beyond the catalyst layer, to form the pore which can be used to predetermine the direction of growth of the nanotube parallel to the surface of the substrate.

8. The nanotube array as claimed in claim 7, in which the electrically insulating layer and/or the further electrically insulating layer is made from one or a combination of the materials silicon nitride and silicon dioxide.

9. The nanotube array as claimed in one of claims 1 to 3, in which, furthermore, at least one of the subregions of the catalyst layer is at least partially surrounded by a layer for preventing diffusion.

10. The nanotube array as claimed in claim 9, in which the layer for preventing diffusion is made from tantalum nitride.

11. The nanotube array as claimed in one of claims 1 to 3, in which the catalyst layer is made from the group consisting of nickel, iron and cobalt.

12. The nanotube array as claimed in one of claims 1 to 3, in which the subregions of the catalyst layer are arranged parallel to one another.

13. The nanotube array as claimed in one of claims 1 to 3, also having a means, which is integrated in the substrate, for recording the electrical resistance of the at least one nanotube.

14. The nanotube array as claimed in one of claims 1 to 3, in which the nanotubes are carbon nanotubes.

* * * * *